(12) United States Patent
Valley et al.

(10) Patent No.: US 9,487,814 B2
(45) Date of Patent: Nov. 8, 2016

(54) STABILIZED FORMULATION FOR LUMINESCENT DETECTION OF LUCIFERASE AND NUCLEOSIDE PHOSPHATES

(71) Applicant: PROMEGA CORPORATION, Madison, WI (US)

(72) Inventors: Michael P. Valley, Fitchburg, WI (US); James J. Cali, Verona, WI (US); Brock Binkowski, Sauk City, WI (US); Christopher Todd Eggers, Madison, WI (US); Keith V. Wood, Madison, WI (US)

(73) Assignee: PROMEGA CORPORATION, Madison, WI (US)

( * ) Notice: Subject to any disclaimer, the term of this patent is extended or adjusted under 35 U.S.C. 154(b) by 0 days.

(21) Appl. No.: 14/186,065

(22) Filed: Feb. 21, 2014

(65) Prior Publication Data

US 2014/0242627 A1  Aug. 28, 2014

Related U.S. Application Data

(60) Provisional application No. 61/783,726, filed on Mar. 14, 2013, provisional application No. 61/767,875, filed on Feb. 22, 2013.

(51) Int. Cl.
*C12Q 1/26* (2006.01)
*C12Q 1/66* (2006.01)

(52) U.S. Cl.
CPC .. *C12Q 1/26* (2013.01); *C12Q 1/66* (2013.01)

(58) Field of Classification Search
None
See application file for complete search history.

(56) References Cited

U.S. PATENT DOCUMENTS

| | | |
|---|---|---|
| 4,235,961 A | 11/1980 | Lundin |
| 4,246,340 A | 1/1981 | Lundin et al. |
| 5,837,465 A | 11/1998 | Squirrell et al. |
| 6,132,983 A | 10/2000 | Lowe et al. |
| 6,171,808 B1 | 1/2001 | Squirrell et al. |
| 6,265,177 B1 | 7/2001 | Squirrell et al. |
| 6,602,677 B1 | 8/2003 | Wood et al. |
| 7,083,911 B2 | 8/2006 | Wood et al. |
| 7,241,584 B2 | 7/2007 | Wood et al. |
| 7,452,663 B2 | 11/2008 | Wood et al. |
| 7,700,310 B2 | 4/2010 | Somberg et al. |
| 7,732,128 B2 | 6/2010 | Wood et al. |
| 7,741,067 B2 | 6/2010 | Hawkins et al. |
| 7,906,298 B1 | 3/2011 | Squirrell et al. |
| 8,030,017 B2 | 10/2011 | Wood et al. |
| 2003/0068801 A1 | 4/2003 | Wood et al. |
| 2006/0183212 A1 | 8/2006 | Wood et al. |
| 2009/0075309 A1 | 3/2009 | Gambhir et al. |
| 2009/0137019 A1 | 5/2009 | Wood et al. |
| 2010/0021949 A1 | 1/2010 | Somberg et al. |
| 2011/0081670 A1 | 4/2011 | Hawkins et al. |
| 2011/0177540 A1 | 7/2011 | Squirrell et al. |
| 2012/0009647 A1 | 1/2012 | Wood et al. |

FOREIGN PATENT DOCUMENTS

| | | |
|---|---|---|
| DE | 19842901 | 3/2000 |
| WO | 01/20002 | 3/2001 |

OTHER PUBLICATIONS

Hawkins et al., Promega, luciferase Assay, 2007, No. 97, p. 30-32.*
Nakamura et al., Biochemical and Biophysical Research Communication, 2005, vol. 331, p. 471-475.*
International Search Report and Written Opinion for Application No. PCT/US2014/017562 dated May 30, 2014 (12 pages).
Nakamura, M. et al., "Construction of a New Firefly Bioluminescence System Using L-Luciferin as Substrate," Tetrahedron Letters 47:7 (2006) pp. 1197-1200.
Lembert, N., "Firefly Luciferase Can Use L-Luciferin to Produce Light," Biochem J. 317, (1996) pp. 273-277.
Ye et al., "Closing and Sequencing of a cDNA for Firefly Luciferase from Photuris pennsylvanica," Biochimica et Biophysica Acta 1339 (1997) pp. 39-52.

\* cited by examiner

*Primary Examiner* — Kade Ariani
(74) *Attorney, Agent, or Firm* — Michael Best & Friedrich LLP

(57) ABSTRACT

Methods, kits and compositions containing a mixture of D-luciferin and L-luciferin for light generation with luciferase are disclosed that have improved stability when stored over time. The mixture of D-luciferin and L-luciferin can be used to detect the presence or amount of ATP or of luciferase in a sample.

16 Claims, 5 Drawing Sheets

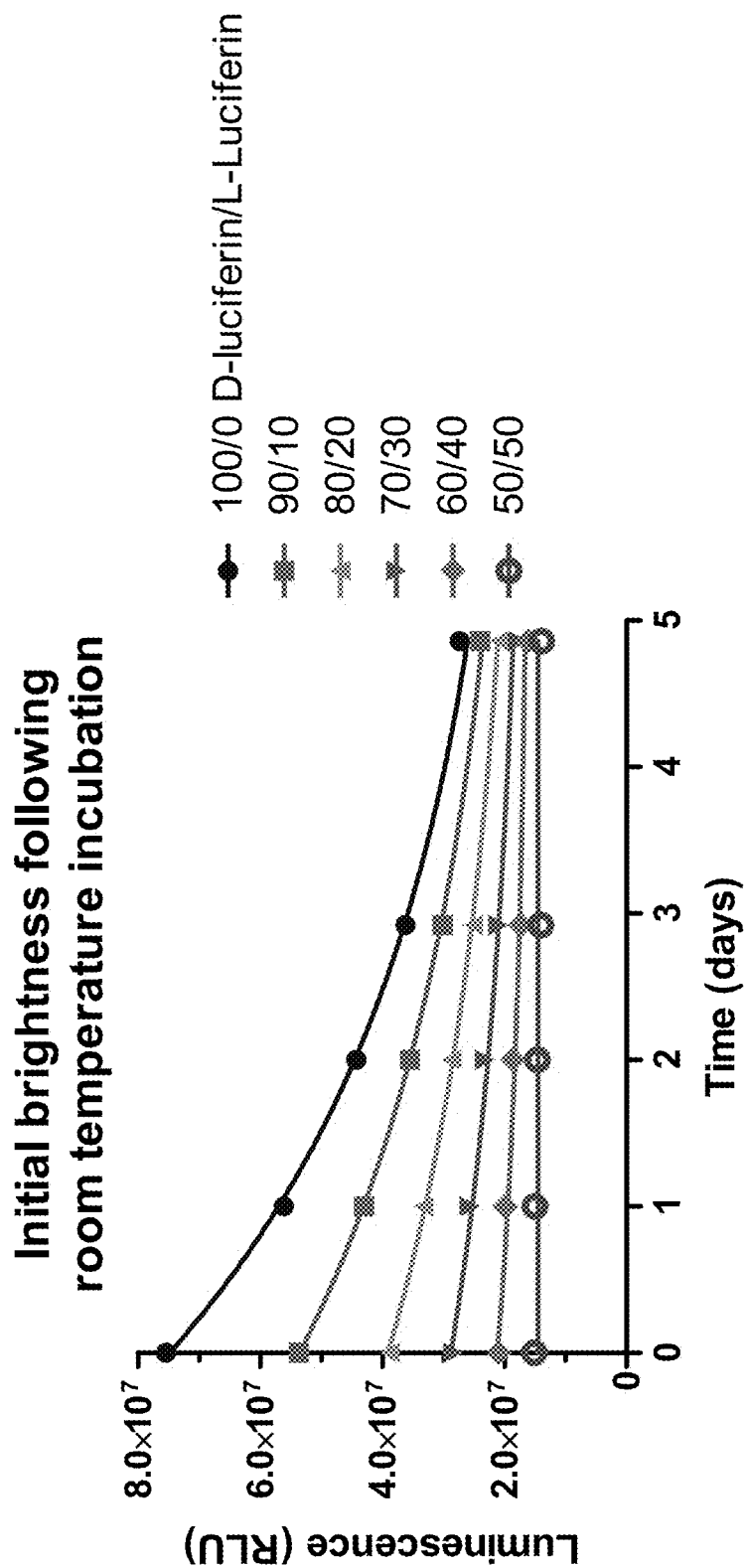

STABILIZED FORMULATION FOR LUMINESCENT DETECTION OF LUCIFERASE AND NUCLEOSIDE PHOSPHATES

CROSS-REFERENCE TO RELATED APPLICATIONS

This application claims priority to U.S. Provisional Application No. 61/767,875, filed Feb. 22, 2013, and U.S. Provisional Application No. 61/783,726, filed Mar. 14, 2013, both of which are incorporated herein by reference in their entirety.

BACKGROUND

Luciferin is a racemic compound that, in solution, racemizes from D-luciferin to L-luciferin or from L-luciferin to D-luciferin. D-luciferin can be utilized as a substrate by the enzyme luciferase to generate light, whereas L-luciferin is largely inhibitory and causes a decrease in luminescence. Slow racemization of D-luciferin to L-luciferin during storage presents problems for assays that exploit the activity of luciferase due to the varying and decreased availability of D-luciferin substrate, and the inhibitory effects of L-luciferin.

FIELD

This disclosure relates to compositions, methods and kits useful for assaying enzymes and metabolites.

SUMMARY

In certain embodiments, a composition is provided comprising a luciferase, L-luciferin and D-luciferin, wherein the composition is essentially free of ATP. In certain embodiments, a composition is provided comprising ATP, L-luciferin and D-luciferin, wherein the composition is essentially free of luciferase.

In some embodiments, a composition is provided comprising D-luciferin, L-luciferin and ATP.

In certain embodiments, a composition is provided comprising a luciferase, L-luciferin and D-luciferin and ATP in which the concentration of L-luciferin exceeds the concentration of D-luciferin.

In some embodiments, a kit is provided which comprises a composition comprising a luciferase, L-luciferin and D-luciferin, the composition being essentially free of ATP and packaged in a container. The kit can include at least one additional component such as one or more detergents such as dodecyltriammonium, hydroxypolyethoxydodecane, potassium phosphate, a defoamer, a buffer, salt(s) and a chelator such as ethylenediaminetetraacetic acid (EDTA).

In some embodiments, a kit is provided which comprises a composition comprising D-luciferin, L-luciferin and ATP, in which the concentration of L-luciferin exceeds the concentration of D-luciferin. The kit can include at least one additional component such as one or more detergents such as dodecyltriammonium, hydroxypolyethoxydodecane, potassium phosphate, a defoamer, a buffer, salt(s) and a chelator such as ethylenediaminetetraacetic acid (EDTA).

In some embodiments, a kit is provided which comprises a composition comprising L-luciferin, D-luciferin and ATP the composition being essentially free of luciferase and packaged in a container. The kit can include at least one additional component such as a buffer, a divalent cation chelator, a magnesium salt, an ionic or non-ionic detergent, a thiol containing compound, such as coenzyme A or DTT, one or more sulfur containing reducing agents or a combination thereof.

In some embodiments, a method for determining the presence or amount of ATP in a sample is provided in which a composition comprising luciferase, L-luciferin and D-luciferin is contacted with a sample, and the luminescence generated is detected and/or measured to determine the presence or amount of ATP in the sample.

In some embodiments, a method, kit or composition for determining the presence or amount of luciferase in a sample is provided in which a composition comprising D-luciferin, L-luciferin and ATP is contacted with a sample which may contain a cell(s) expressing a luciferase. The luminescence generated is then detected and/or measured to determine the presence or amount of luciferase in the sample. The sample containing a cell(s) expressing luciferase can be a lysed cell(s), a crude cell extract or a clarified cell extract.

In some embodiments, a method for detecting luciferase activity from a cell expressing a luciferase is provided in which luciferase is expressed in the cell, and the cell is contacted with a mixture comprising L-luciferin and D-Luciferin at a ratio of L-Luciferin to D-Luciferin of at least about 5:95 to about 75:25. In some embodiments, the mixture comprises L-luciferin and D-Luciferin at a ratio of L-Luciferin to D-Luciferin of at least about 5:95 to about 55:45, or at least about 5:95 to about 50:50. The luminescence generated is then detected and/or measured to determine the presence or amount of luciferase in the cell.

In some embodiments, a method for detecting or quantifying a nucleoside phosphate such as ATP, or a source of ATP, in a cell or other sample is provided in which the cell or sample is contacted with a mixture comprising L-luciferin and D-Luciferin at a ratio of L-Luciferin to D-Luciferin of at least about 0.5:1 to about 2:1 and a luciferase. The luminescence generated is then detected and/or measured to determine the presence or amount of nucleoside phosphate in the cell.

In some embodiments, a method for performing a luciferase reaction is provided. A mixture comprising L-luciferin and D-Luciferin is stored for a period of time at a temperature from about 0° C. to about 25° C. When the mixture is used in a luciferase activity assay, the light output, i.e., luminescence, is measured. The mixture is permitted to be contacted with a sample, or part of a sample, containing or expressing luciferase, ATP or a source of ATP, to form a reaction assay. The luminescence generated in the reaction assay is then detected. The reaction assay containing a mixture that has been stored for a period of time generates a light output that, in certain embodiments, is at least about 50% or at least about 90% of the light output of a comparable reaction assay containing the mixture at the start of the storage period (time t=0). In certain embodiments, the storage time period may be at least about 30 minutes, at least about 1 hour, at least about 4 hours or longer.

In some embodiments, a method for formulating components for a luciferase reaction is provided. D-Luciferin and L-luciferin are combined to form a mixture, which is stored for a period of time, such as a period of about 1, 2, 3 or 4 hours or 1 or 2 weeks at a temperature from about 0° C. to about 25° C. The mixture allows for the generation of light output, i.e., luminescence, when used in a luciferase activity assay such that the light output generated after the period is at least about 50% or at least about 90% of the light output at the beginning of the period.

Other aspects of the invention will become apparent by consideration of the detailed description and accompanying drawings

DESCRIPTION OF THE DRAWINGS

FIG. 5 is a graph depicting the Effect of Different D-/L-luciferin (5'-fluoroluciferin) ratios on the stability of a luciferase reporter assay reagent.

DETAILED DESCRIPTION

Figure 1:
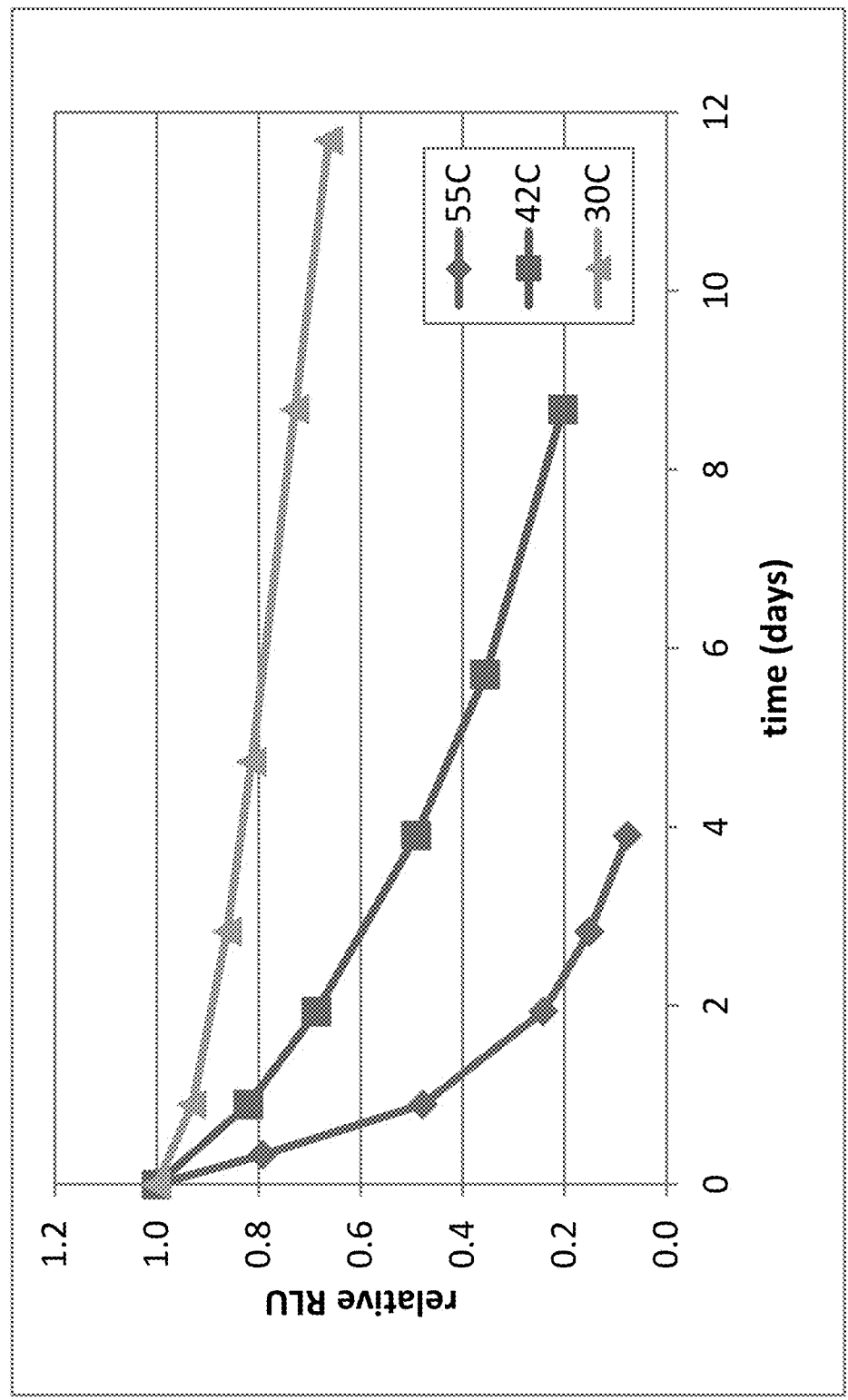
FIG. 1 is a graph depicting luminescence detected from assays containing L-luciferin and D-luciferin after storage of the luciferin mixture at different temperatures for different times.

Racemization of D-Luciferin to L-luciferin in a liquid formulation during storage results in a mixture of the D- and L-enantiomers of luciferin, of which D-luciferin can be utilized as a substrate by a luciferase enzyme to generate light. The unpredictability in the amount of D-luciferin available for luciferase is problematic for assays that depend upon measuring luciferase activity, such as those that measure the amount of metabolites, e.g., ATP, in a sample. The presence of L-luciferin in an assay may also be problematic as it acts as an inhibitor of the luciferase enzyme.

In some embodiments, a composition comprising both D-luciferin and L-luciferin provided in a mixture is disclosed. In some embodiments, the composition can be used with luciferase to measure the activity of an ATP-utilizing enzyme, e.g., a kinase; to measure the amount or concentration of ATP; to measure a particular metabolite in a sample through the intermediary production of ATP; to provide stable measurements over a period of time or a combination thereof. In some embodiments, the composition can be used to detect or measure the amount of luciferase expressed by a cell(s). Surprisingly, compositions containing a mixture of D-luciferin and L-luciferin show superior stability over compositions containing substantially pure D-luciferin, or compositions comprising D-luciferin and substantially no L-luciferin, such as comprising trace amounts of L-luciferin, with minimal decrease in assay performance. For example, superior stability may occur when L-luciferin is present in at least about 1%, in at least about 5%, in at least about 10%, in at least about 15%, in at least about 25%, in at least about 30%, in at least about 35%, at least about 40%, in at least about 45%, at least about 50%, in at least about 55%, at least about 60%, in at least about 65%, at least about 70% or at least about 75% or more of the total luciferin present, or when the amount of L-luciferin exceeds the amount of D-luciferin present. Metabolites that can be measured through the intermediary production of ATP include, without limitation, nucleoside diphosphates such as adenosine diphosphate (ADP), guanosine diphosphate (GDP), uridine diphosphate (UDP), as well as adenosine monophosphate (AMP). In certain embodiments, the composition comprising the mixture of D-luciferin and L-luciferin optionally comprises luciferase and may optionally be substantially free of ATP, other nucleoside triphosphates, nucleoside diphosphates, nucleoside monophosphates or combinations thereof In other embodiments, the composition comprising the mixture of D-luciferin and L-luciferin, for example a mixture wherein the concentration of L-luciferin exceeds the concentration of D-luciferin, may optionally comprise ATP.

D-luciferin includes the compound (D-(−)-2-(6'-hydroxy-2'-benzothiazolyl)-thiazoline-4-carboxylic acid), and L-luciferin includes the compound (L-(−)-2-(6'-hydroxy-2'-benzothiazolyl)-thiazoline-4-carboxylic acid) and their salt forms. As used herein, whether in D- or L-isomeric form, luciferin includes salt forms such as potassium salt, sodium salt, or other alkaline or alkaline earth salts, the free acid as well as luciferin derivatives and their salt forms such as chloroluciferin and fluoroluciferin e.g., 5'-fluoroluciferin, 7'-fluoroluciferin and 5'-chloroluciferin and 7'-chloroluciferin and others disclosed in U.S. published application 2009-0075309, the entire disclosure of which is herein incorporated by reference.

D-Luciferin and L-luciferin (D-luciferin:L-luciferin) may be present at a ratio of least about 0.25:1, at least about 0.3:1, at least about 0.4:1, at least about 0.5:1, at least about 0.6:1, at least about 0.7:1, at least about 0.8:1, at least about 0.9:1, at least about 1:1, and less than about 4:1, less than about 3.75:1, less than about 3.5:1, less than about 3.25:1, less than about 3:1, less than about 2.75:1, less than about 2.5:1, less than about 2.25:1, less than about 2:1, less than about 1.9:1, less than about 1.8:1, less than about 1.7:1, less than about 1.6:1, less than about 1.5:1, less than about 1.4:1, less than about 1.3:1, less than about 1.25:1, less than about 1.2:1 or less than about less than about 1.1:1.

L-Luciferin and D-luciferin (L-luciferin:D-luciferin) may be present at a ratio of at least about 0.1:99.9, least about 1:99, at least about 2:98, at least about 3:97, at least about 4:96, at least about 5:95, at least about 10:90, at least about 15:85, at least about 20:80, at least about 25:75, at least about 30:70, at least about 35:65, at least about 40:60, at least about 45:55, at least about 49:51, or at least about 50:50, and less than about 99:0.1, less than about 99:1, less than about 98:2, less than about 97:3, less than about 96:4, less than about 95:5, less than about 90:10, less than about 85:15, less than about 80:20, less than about 75:25, less than about 70:30, less than about 65:35, less than about 60:40, less than about 55:45, less than about 51:49, or less than about 50:50.

The mixture comprising D-luciferin, L-luciferin and optionally a luciferase may be substantially free of or exclude any amount of nucleoside triphosphates, nucleoside diphosphates or any combination thereof For example, the mixture comprising D-luciferin, L-luciferin and optionally a luciferase may be substantially free or exclude any amount of ATP, GTP, CTP, mSUTP, UTP or combination thereof. The mixture comprising D-luciferin, L-luciferin and optionally a luciferase may be substantially free or exclude any amount of ADP, GDP, CDP, mSUDP, UDP or combination thereof. The mixture comprising D-luciferin, L-luciferin and optionally luciferase may contain less than about 50 μM ATP, less than about 10 μM ATP, less than about 5 μM ATP, less than about 1 μM ATP, less than about 0.5 μM ATP, less than about 0.1 μM ATP, less than about 0.05 μM ATP, less than about 0.01 μM ATP, less than about 0.005 μM ATP, or less than about 0.001 μM ATP, or less than about 0.0001 μM ATP or other nucleoside triphosphate described herein.

In some embodiments, the mixture comprising D-luciferin, L-luciferin and optionally luciferase may contain at least 0.005 µM ATP, at least about 0.01 ATP, at least about 0.05 µM ATP, at least about 0.1 µM ATP, at least about 0.5 µM ATP, at least about 1 µM ATP, at least about 5 µM ATP, at least about 10 µM µM ATP, at least about 50 µM ATP and less than about 10 mM ATP, less than about 5 mM ATP, less than about 4 mM ATP, less than about 3 mM ATP, less than about 2 mM ATP, less than about 1 mM ATP, less than about 0.5 mM ATP. For example, such a mixture may comprise a ratio of L-luciferin:D-luciferin that is greater than 1:1, greater than 1.1:1, greater than 1.2:1, greater than 1.3:1, greater than 1.4:1, greater than 1.5:1, greater than 1.6:1, greater than 1.7:1, greater than 1.8:1, greater than 1.9:1, greater than 2:1, greater than 2.25:1, greater than 2.5:1, greater than 2.75:1, or greater than 3:1.

The mixture comprising D-luciferin and L-luciferin may optionally substantially include any amount of nucleoside triphosphates, e.g., ATP, GTP, CTP, nucleoside diphosphates, e.g., ADP, GDP, CDP or any combination thereof The mixture comprising D-luciferin and L-luciferin remains stable over long periods of time, where stability is measured by light output when the mixture is used in a luciferase activity assay. In contrast to conventional formulations, which can show about a 10% loss of activity after 8 hours at 22° C. or after 4 days at 4° C., the present formulations exhibit increased stability. At least about 50%, at least about 55%, at least about 60%, at least about 65%, at least about 70%, at least about 75%, at least about 80%, at least about 85%, at least about 90%, or at least about 95% of the original activity (where original activity is measured in a luciferase activity assay at T=0 under a given set of conditions and the subsequent activity is measured under substantially the same conditions at a later time point) is detected after a period of storage of at least about at least about 8 hours, at least about 10 hours, at least about 12 hours, at least about 18 hours, at least about 1 day, at least about 2 days, at least about 3 days, at least about 4 days, at least about 5 days, at least about 1 week, at least about 2 weeks, at least about 3 weeks, at least about 4 weeks, at least about 1 month, at least about 2 months, at least about 3 months, at least about 4 months, at least about 5 months, at least about 6 months, at least about 9 months, at least about 12 months, at least about 18 months, at least about 2 years, at least about 3 years, at least about 4 years or longer, when stored, for example, at a temperature of about 4° C. (for example from about 1° C. to about 6° C.) or about 20° C. to 25° C., such as about 22° C. (for example from about 20° C. to about 25° C.). For example, methods, compositions and kits described herein using about a 50:50 mixture of L-luciferin and D-luciferin will have at least about 50% of the original activity remaining after incubation of about or at least about 2 months at a temperature from about 20° C. to about 25° C.

A luciferase activity assay includes, for example, luciferase, luciferin (e.g. 1 mM), ATP (e.g., 3 mM), $MgSO_4$ (e.g., 15 mM) in buffer at a pH that is optimal for the enzyme used. Other optional components may be present to optimize or stabilize the activity of the luciferase used. Examples of luciferase activity assays are described herein in the examples. In some embodiments, the luciferase may be purified, or it may be expressed in the sample, e.g., a reporter gene.

Kits, methods and compositions comprising a mixture of D-luciferin and L-luciferin are provided herein. The kits, methods and compositions may include one or more luciferases or may be used to assay luciferase in a transformed prokaryotic or transfected eukaryotic cell using a luciferase reporter assay. The cell can be, for example, a bacterial cell, a mammalian cell, a plant cell or a fungal cell.

Luciferases, which utilize luciferin as a substrate, include beetle luciferases, such as that of the common firefly (family Lampyridae). Beetle luciferases are often referred to as firefly luciferases in the literature; however, firefly luciferases are actually a subgroup of the beetle luciferase class. Beetle luciferases also include click beetle luciferase, such as from *Pyrophorus plagiophthalamus*. Beetle luciferases may be purified from the lanterns of the beetles themselves or from protein expression systems well known in the art.

Beetle luciferases, particularly firefly luciferase from the North American firefly *Photinus pyralis* or *Photuris pennsylvanica*, are well known in the art. The *P. pyralis* luciferase (LucPpy) consists of approximately 550 amino acids (61 kDa) as calculated by the protein encoded by the nucleotide sequence of the gene. The *Photuris pennsylvanica* firefly luciferase (LucPpe2) consists of 545 amino acid residues (GenBank 2190534; Ye et al., 1997). Mutant luciferases, e.g., thermostable and/or chemostable, derived from LucPpe2 may include LucPpe2m78 (also known as 78-0B10), LucPpe2m90 (also known as 90-1B5), LucPpe2m133 (also known as 133-1B2) and LucPpe2m146 (also known as 146-1H2). However, any luciferase that meets the limitations set forth herein may be used in the composition, method and kits of the invention. A method of deriving thermostable and/or chemostable luciferases such as LucPpe2m78, LucPpe2m90, LucPpe2m133, and LucPpe2m146 is disclosed in PCT/US99/30925.

Isolated and/or purified luciferases can be used. Contaminant components of the luciferase natural environment are materials that would typically interfere with the luciferase assay, and may include enzymes, hormones, and other proteinaceous or non-proteinaceous materials. One technique to ascertain purity is applying SDS-PAGE analysis under non-reducing or reducing conditions using Coomassie blue or silver stain.

Luciferases useful in the compositions, kits and methods of the invention include those that generate a stable signal and/or are thermostable and/or chemostable, i.e., they yield enhanced duration of luminescence in a luciferase reaction defined as less than 50% loss of luminescence per 30 minutes relative to the luminescence at the time the luciferase reaction was initiated or greater enzyme stability at higher temperatures. Exemplary luciferases are disclosed in U.S. Pat. Nos. 6,132,983; 6,171,808; 6,265,177; 6,602,677; 7,241,584; 7,906,298; and 8,030,017; and U.S. Patent Application Publication Nos. 2003-0068801, 2006-0183212, 2009-0137019, 2011-0177540, and 2012-0009647, the disclosure of each of which is herein incorporated by reference in its entirety.

Luciferases in the compositions, kits and methods of the invention also include luciferases that generate a "flash" signal and have a half-life for light output of less than about 30 minutes, less than about 25 minutes, less than about 20 minutes, less than about 15 minutes, less than about 10 minutes, less than about 5 minutes, less than about 4 minutes, less than about 3 minutes, less than about 2 minutes, or less than about 1 minutes.

Luciferases include those that display increased thermostability for at least 2 hours at 50° C., or at least 5 hours at 50° C. Thermostable luciferases which, when solubilized in a suitable aqueous solution, include those having a stability half-life greater than about 2 hours at about 50° C., greater than about 5 hours at 50° C., greater than about 10 hours at 50° C., greater than about 5 hours at about 60° C., greater than about 10 hours at about 60° C., greater than about 24 hours at about 60° C., greater than about 3 months at about 22° C. or greater than about 6 months at 22° C.

In certain embodiments, the amount of luciferase present in a reaction mixture comprising a racemic mixture of L-luciferin and D-luciferin, as described herein, may be increased to provide a light output that is substantially equivalent to a similar reaction mixture that does not comprise a racemic mixture of L-luciferin and D-luciferin. For example, the amount of luciferase may be increased to at least about 120%, at least about 150%, at least about 200% (2-fold), at least about 250%, at least about 300%, at least about 350%, at least about 400%, at least about 500% (5-fold), at least about 600%, at least about 700%, at least about 800%, at least about 900% or at least about 1000% (10-fold) of the luciferase amount in the reaction mixture that does not comprise a racemic mixture of L-luciferin and D-luciferin to achieve a substantially equivalent light output.

In certain embodiments, the compositions, methods and kits described herein provide an increased half-life of the luminescent signal generated during a luciferase reaction. The compositions, methods and kits described herein containing a mixture of D-luciferin and L-luciferin may increase the half-life of the luminescent signal (luminescence generated during a luciferase reaction) by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 125%, at least about 150%, at least about 175%, at least about 200%, at least about 250%, at least about 300%, or at least about 350% , at least about 400%, at least about 450%, or at least about 500%, compared with the luminescent signal generated from a luciferase reaction that comprises substantially pure D-luciferin, or D-luciferin and substantially no L-luciferin, such as comprising trace amounts of L-luciferin. In some embodiments at least about a 2-fold, at least about a 3-fold, at least about a 4-fold, at least about a 5-fold, at least about a 6-fold, at least about a 7-fold, at least about a 8-fold, at least about a 9-fold, at least about a 10-fold, at least about a 12-fold, at least about a 15-fold, or at least about a 20-fold increase in luminescent signal half-life is achieved compared with the luminescent signal generated from a luciferase reaction that comprises substantially pure D-luciferin, or D-luciferin and substantially no L-luciferin, such as comprising trace amounts of L-luciferin.

The light output can be measured in relative light units (RLUs). In some embodiments, the initial light output of the luminogenic reaction is lower when a mixture of D-luciferin and L-luciferin is used. For example, the initial light output may be less than about 95%, less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, or less than about 5% of the initial light output compared with a luminogenic reaction that comprises substantially pure D-luciferin, or D-luciferin and substantially no L-luciferin, such as comprising trace amounts of L-luciferin. In some embodiments, the lower initial light output is accompanied by an increased half-life of the luminogenic reaction, as described herein.

In kits, methods and compositions described herein, luciferase may be provided in a solution, such as an aqueous solution, containing L-luciferin and D-luciferin, or may be provided in a desiccated or dried form, for example, in a container separate from the D-luciferin and L-luciferin, which is solubilized prior to use. In some embodiments, luciferase is provided in a container separate from the D-luciferin and L-luciferin in solubilized form. The amount of luciferin, whether D-luciferin, L-luciferin or a combination of D-luciferin and L-luciferin, included in the compositions, kits and methods described herein can be at least about 1 nM, at least about 5 nM, at least about 10 nM at least about 50 nM at least about 100 nM, at least about 0.5 µM, at least about 1 µM, at least about 5 µM, at least about 10 µM, at least about 25 µM, at least about 50 µM, at least about 100 µM, at least about 250 µM, at least about 0.5 mM, at least about 1 mM, and less than about 50 mM, less than about 40 mM, less than about 30 mM, less than about 30 mM, less than about 10 mM, less than about 5 mM, less than about 4 mM, less than about 3 mM, or less than about 2 mM.

Kits, compositions and methods described here may include, in addition to a mixture of D-luciferin and L-luciferin described herein, one or more additional components, such as luciferase; a buffer such as citric acid or citrate buffer, MES, 1,4-Piperazinediethanesulfonic acid, or HEPES; inorganic phosphate, for example, in the form pyrophosphate or potassium phosphate; a chelator such as EDTA, CDTA or 1,2-Diaminocyclohexanetetraacetic acid; a salt such as sodium fluoride, magnesium sulfate; a surfactant or detergent such as TERGITOL® (e.g. a non-ionic nonylphenol ethoxylate), dodecyltrimethylammonium bromide (DTAB) or THESIT® (hydroxypolyethoxydodecane); a defoamer such as INDUSTROL® DF204 (organic defoamer) or MAZU® DF (silicone defoamer); a protein stabilizer such as gelatin, PRIONEX® 10% (gelatin, Type A) or albumin (e.g. BSA, HSA) or glycerol; adenosine triphosphate (ATP) or adenosine monophosphate (AMP). Other components may include polyethylene glycol, polyvinyl pyridine, crown ether, or cyclodextrin. Additional components may include, for example, one or more of, thiol compounds, such as coenzyme A, reducing agents such as dithiothreitol (DTT), or sulfur containing compounds acting as reductants, such as sulfite, thiosulfate.

Detergents that may be included in the kits, compositions and methods include cationic, anionic, non-ionic or zwitterionic detergents. The detergent can comprise, for example, Tergitol® detergent (polyglycol ether (nonionic)), Brij 35® detergent (polyoxyethylene 23 lauryl ether), Brij 58® detergent (polyoxyethylene 20 cetyl ether ($HO(CH_2CH_2O)_{20}C_{16}H_{33}$)), Triton X-100® detergent (4-(1,3,3-tetramethylbutyl)phenyl-polyethylene glycol (t-Oct-$C_6H_4$—$(OCH_2CH_2)_x$ OH, x=9-10)), Triton X-305® detergent (4)-(1,1,3,3-tetramethylbutyl)phenyl-polyethylene glycol), Triton N1010 detergent (polyoxyethylene-9,10 branched nonylphenyl ether), CHAPS® detergent (3-[(3-cholamidopropyl)dimethylammonio]-1-propanesulfonate), Chapso® detergent (3-([3-cholamidopropyl]dimethylammonio)-2-hydroxy-l-propanesulfonate), Bigchap® detergent (N,N-bis(3-D-Gluconamidopropyl)cholamide), Thesit® detergent (polyethylene glycol 400 dodecyl ether ($HO(CH_2CH_2O)_n(CH_2)_{11}CH_3$)), Pluronic L64® detergent (poly(ethylene glycol)-block-poly(propylene glycol)-block-poly(ethylene glycol)), Rhodasurf 870® detergent (polyethoxylated (20) oleyl alcohol), Chemal LA-9® detergent (polyoxyethylene 9 lauryl alcohol), Sulfonyl 465® detergent (2,4,7,9-tetramethyl-5-deceyne-4,7-diol ethoxylate 10), deoxycholate, CTA 3, Pierce C08® detergent (C8=Octyl-β-D-glucopyranoside), or Pierce C100 detergent (n-decyl-.beta.-D-maltoside (C10 alkyl side chain)).

The mixture containing D-luciferin and L-luciferin used in the methods, kits and compositions described herein or the assays described herein which utilize the D-luciferin and L-luciferin can have a pH of at least about 5, at least about 5.1, at least about 5.2, at least about 5.3., at least about 5.4, at least about 5.5, at least about 5.6, at least about 5.7, at least about 5.8, at least about 5.9, at least about 6, at least about 6.1, at least about 6.2, at least about 6.3, at least about 6.4, at least about 6.5, at least about 6.6, at least about 6.7, at least about 6.8, at least about 6.9, at least about 7, at least about 7.1, at least about 7.2, at least about 7.3, at least about 7.4, at least about 7.5, at least about 7.6, at least about 7.7, at least about 7.8, at least about 7.9, at least about 8, at least about 8.1, at least about 8.2, at least about 8.3, at least about 8.4, or at least about 8.5 and less than about 9, less than about 8.9, less than about 8.8, less than about 8.7, less than about 8.6, less than about 8.5, less than about 8.4, less than about 8.3, less than about 8.2, less than about 8.1, less than about 8, less than about 7.9, less than about 7.8, less than about 7.7, less than about 7.6, less than about 7.5, less than about 7.4, less than about 7.3, less than about 7.2, less than about 7.1, less than about 7, less than about 6.9, less than about 6.8, less than about 6.7, less than about 6.6, or less than about 6.5. The pH can be maintained in the mixture composition or assay to provide an environment that facilitates bright luminescence at a fast rate, such as a pH of from about 8 to 9, or a slower rate of luminescence providing more sustained luminescence, such as a pH of less than about 7.5 or less than about 7.

The D-Luciferin and L-luciferin may be combined together at any of the ratios described herein prior to being stored for a period of time. Luciferase, ATP, or any other component of the kits or compositions disclosed herein, may be optionally combined with a mixture of D-luciferin and L-luciferin prior to storage. The mixture may be stored at a temperature of at least about −85° C., at least about −80° C., at least about −75° C., at least about −50° C., at least about −40° C., at least about −30° C., at least about −25° C., at least about −20° C., at least about 0° C., at least about 1° C., at least about 2° C., at least about 3° C. or at least about 4° C. and less than about 45° C., less than about 40° C., less than about 38° C., less than about 35° C., less than about 30° C., less than about 25° C., less than about 22° C., less than about 21° C., less than about 20° C., less than about 15° C., less than about 10° C., less than about 8° C., or less than about 6° C. for a time period. The time period for storage may be at least about 4 hours, at least about 8 hours, at least about 12 hours, at least about 1 day, at least about 1 week, at least about 2 weeks, at least about 4 weeks, at least about 2 months, at least about 3 months, at least about 4 months, at least about 6 months, or at least about 12 months. The amount of D-luciferin remaining after the period of storage may be at least about 99%, at least about 98%, at least about 95%, at least about 90%, at least about 85%, at least about 80%, at least about 75%, or at least about 70%, at least about 65%, at least about 60%, at least about 55%, at least about 54%, at least about 53%, at least about 52%, or at least about 51% of the initial amount of D-luciferin in the mixture prior to storage. The amount of D-luciferin remaining after the period of storage may be at least about 101%, at least about 105%, at least about 110%, at least about 115%, at least about 120%, at least about 125%, at least about 130%, at least about 140%, at least about 150%, at least about 175%, at least about 200%, at least about 250%, at least about 300%, at least about 400%, at least about 500%, at least about 750%, at least about 1000%, of the initial amount of D-luciferin in the mixture prior to storage, for example, if the formulation comprises more L-luciferin than D-luciferin prior to storage.

The compositions and kits disclosed herein may be used to assay the presence or amount of ATP in a sample by a luciferase-luciferin reaction which generates luminescence. The ATP may be present in the sample following an ATP-utilizing reaction, e.g., kinase reaction, such that the amount of ATP in the sample and luminescence generated is inversely proportional to the amount of activity of the ATP-utilizing enzyme. The sample may contain intact cells, may be a crude or clarified cell lysate or may comprise a purified enzyme which generates or uses ATP.

The compositions and kits disclosed herein may be used to assay the presence or amount of luciferase in a sample. The luciferase may be present in the sample following transfection, e.g., transient or stable, of a luciferase gene, e.g., a reporter gene. The sample may contain intact cells, crude or clarified cell lysate or comprise a whole animal, such as for whole animal imaging. The luciferase may be present in the sample following expression of the luciferase coding sequence in cell-free extract, e.g., rabbit reticulocyte lysate or wheat germ translation systems.

It is to be understood that the invention is not limited in its application to the details of construction and the arrangement of components set forth in the description or illustrated in the following drawings. The invention is capable of other embodiments and of being practiced or of being carried out in various ways.

It is to be understood that any numerical range recited in this specification includes all values from the lower value to the upper value. For example, if a concentration range is stated as 1% to 50%, it is intended that values such as 2% to 40%, 10% to 30%, or 1% to 3%, etc., are expressly enumerated in this specification. It is also to be understood that any numerical range recited in this specification includes all values from at least the lower value without an upper limit, and all values up to the upper value without a lower limit. These are only examples of what is specifically intended, and all possible combinations of numerical values between and including the lowest value and the highest value enumerated are to be considered to be expressly stated in this application.

It also is to be understood that the invention is not limited in its application to the details of construction and the arrangement of components set forth in the description. Also, it is to be understood that the phraseology and terminology used in this specification is for the purpose of description and should not be regarded as limiting. The use of the terms "a" and "an" and "the" and similar referents in the context of describing the invention are to be construed to cover both the singular and the plural, unless otherwise indicated in this specification or clearly contradicted by context. The terms "comprising," "having," "including," and "containing" are to be construed as open-ended terms (i.e., meaning "including but not limited to") unless otherwise noted. All methods described in this specification can be performed in any suitable order unless otherwise indicated in this specification or otherwise clearly contradicted by context. Patent applications, patents and literature references cited here are specifically and completely incorporated by reference in their entirety. Where inconsistent interpretations are possible, the present disclosure controls.

The use of any and all examples, or exemplary language (e.g., "such as") provided here, is intended merely to illustrate aspects and embodiments of the disclosure and does not limit the scope of the claims.

EXAMPLE 1

Accelerated Stability 5 mM L-luciferin was dissolved in CellTiter-Glo (an ATP detection reagent containing Ultra-Glo luciferase and 5 mM D-luciferin; Promega Corporation). Aliquots were placed at various temperatures for various lengths of time and then stored at −80° C. All samples were thawed to room temp at the same time and then mixed 1:1 with 1 µM ATP in water. Luminescence (RLUs) was measured after 10 min. The results are depicted in FIG. 1.

From the decay rates at higher temperature, the Arrhenius equation was used to calculate the rates of decay at lower temperatures. At 22° C., a 10% loss in performance was calculated to occur in 8.6 days. At 4° C., a 10% and 50% loss at 4.2 months and 2 years, respectively, was calculated. At −20° C., a 10% loss in 20 years was calculated.

EXAMPLE 2

Real-time Stability at 22° C.

Figure 2:
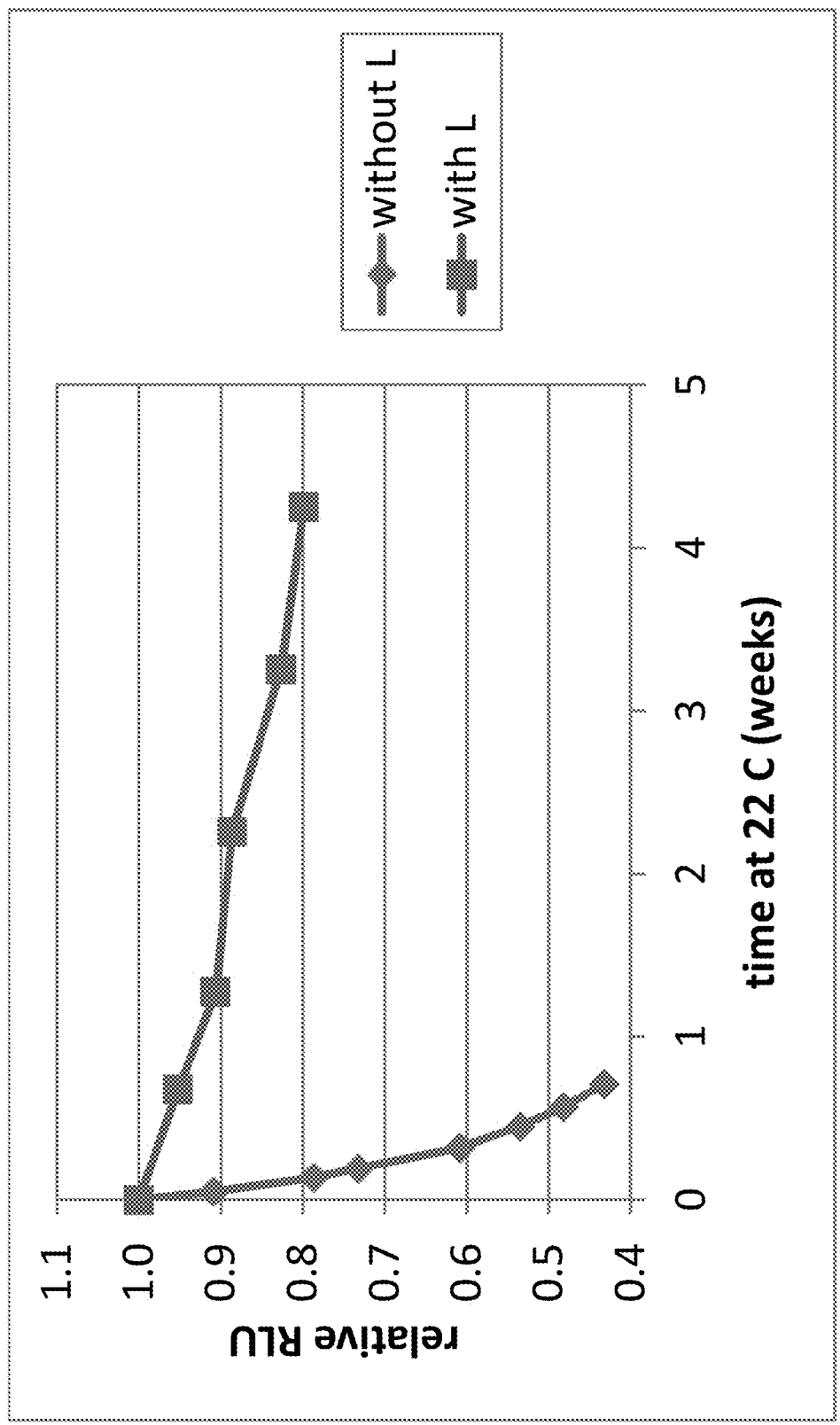
FIG. 2 is a graph depicting luminescence detected from assays containing D-luciferin, or both D-luciferin and L-Luciferin after storage of the luciferin for various times.

Aliquots of CellTiter-Glo with and without 5 mM L-luciferin were placed at 22° C. for various lengths of time and then stored at −80° C. All samples were thawed to room temp at the same time and then mixed 1:1 with 1 µM ATP in water Luminescence (RLUs) was measured after 10 min. The results are depicted in FIG. 2.

At 22° C., a 10% change in performance occurred in about 12 hours or about 2 weeks for CellTiter-Glo without and with L-luciferin, respectively.

EXAMPLE 3

Comparison of Luciferin and 5'-Fluoroluciferin 5 mM L-isomer luciferin or fluoroluciferin was dissolved in a reagent (500 mM MES, pH6, 400 mM KCl, 3 mM CDTA, 20 mM MgSO4, 2 mM NaF, 15 µM tetrasodium pyrophosphate, 2% Thesit, 1% DTAB, 0.2% Mazu, and 0.21 mg/ml Ultra-Glo) containing 5 mM of the respective D-isomer. Each reagent, including CellTiter-Glo, was then mixed 1:1 with 2 µM ATP in water, and luminescence (RLUs) measured over time. The results are depicted in Table 1.

TABLE 1

| luciferin | 5'-fluoro | RLU @ 10' | half-life (hrs) |
|---|---|---|---|
| D | | 31,685,833 | 1.72 |
| D + L | | 7,229,377 | 6.66 |
| | D | 27,391,967 | 2.75 |
| | D + L | 12,016,733 | 5.56 |
| | CTG | 5,181,023 | 5.25 |

Although there is only a modest difference in light output when comparing the D-isomers, the isomeric mixture of 5'-fluoroluciferin is substantially brighter than that of luciferin with roughly the same signal half-life.

EXAMPLE 4

Figure 3:
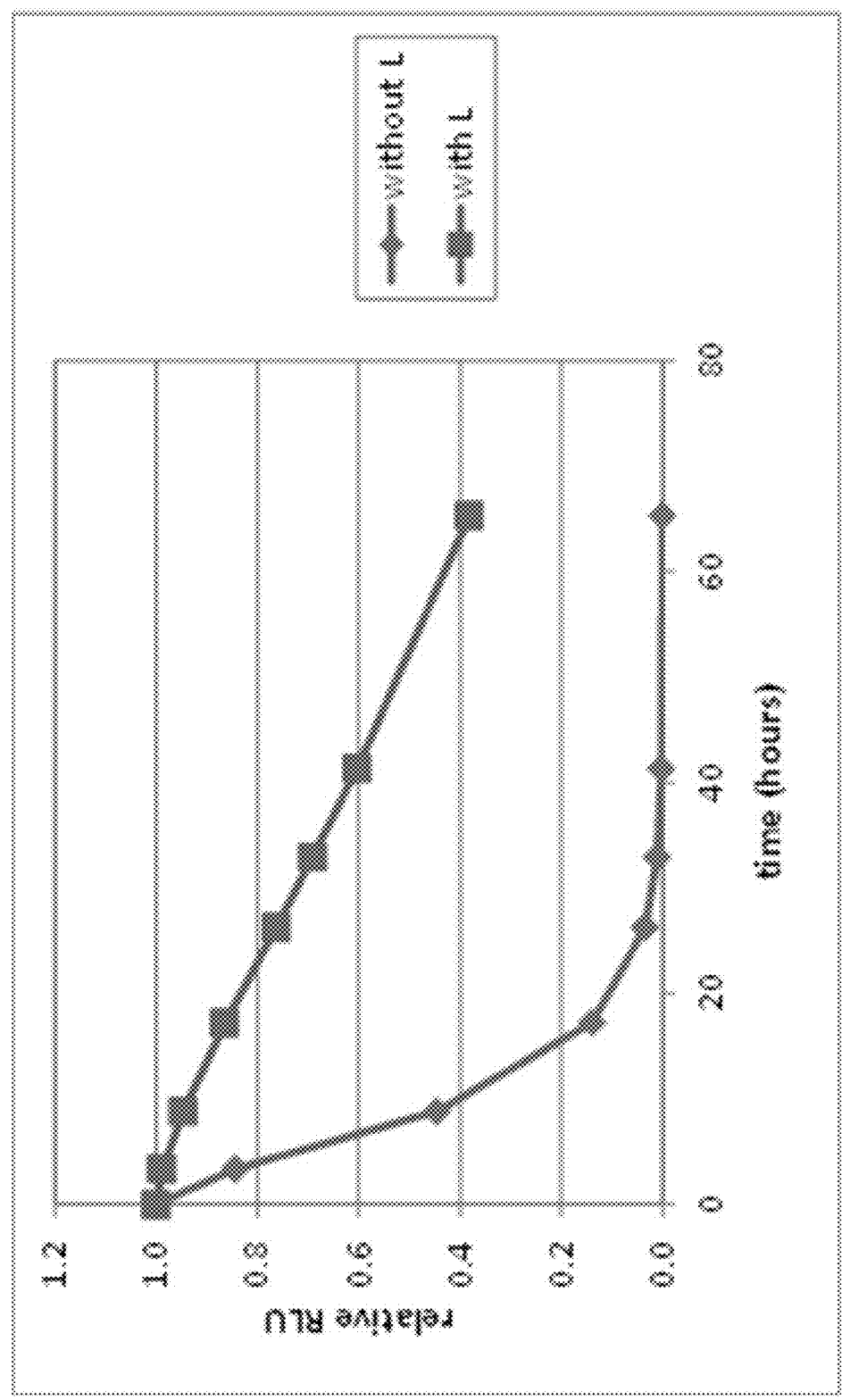
FIG. 3 is a graph depicting luminescence detected from assays containing D-luciferin, or both D-luciferin and L-Luciferin after storage of the luciferin for various times.

Enhanced Stability in a Reagent Containing Native Firefly Luciferase 1 mM L-luciferin was dissolved in a reagent (50 mM MgAcetate, 25 mM TrisAcetate, pH 7.75, 0.1 mM EDTA, 0.002% azide, 0.5 mM DTT, 1.3 mg/ml BSA) containing 1 mM D-luciferin and 13.54 µg/ml native firefly luciferase (QuantiLum® recombinant luciferase, Promega, Madison Wis.). Aliquots were placed at 22° C. for various lengths of time and then stored at −80° C. All samples were thawed to room temp at the same time and then mixed 1:1 via injection with 20 nM ATP in water. After a 10 second delay, luminescence (RLUs) was measured and integrated for 10 seconds. The results are depicted in FIG. 3.

At 22° C., a 10% change in performance occurred in about 5 hours and about 50 hours with reagents without or with the L-isomer of luciferin, respectively.

EXAMPLE 5

Effect of Different D-/L-luciferin Ratios in Luciferase Reporter Assay Reagent on Luminescence and Signal Half-Life HEK293 cells stably expressing firefly luciferase (CMV-Fluc) were plated in white 96-well plates at $2.5 \times 10^5$ cells/ml in 100 µl complete media (DMEM +10% FBS+1×NEAA (non-essential amino acid)). The cells were then incubated overnight at 37° C., 5% $CO_2$. After the overnight incubation, the plate was equilibrated to 22° C. 100 µl of firefly luciferase reporter assay reagents containing 1 mM luciferin at 100:0; 95:5; 90:10; 85:15; 80:20; or 75:25 D-/L-5'-fluoroluciferin were added to the cells (n=3) and incubated with mixing for 3 minutes. Luminescence was measured every 3 minutes for 5 hours on a GloMax® Multi+ at 22° C.

Figure 4:
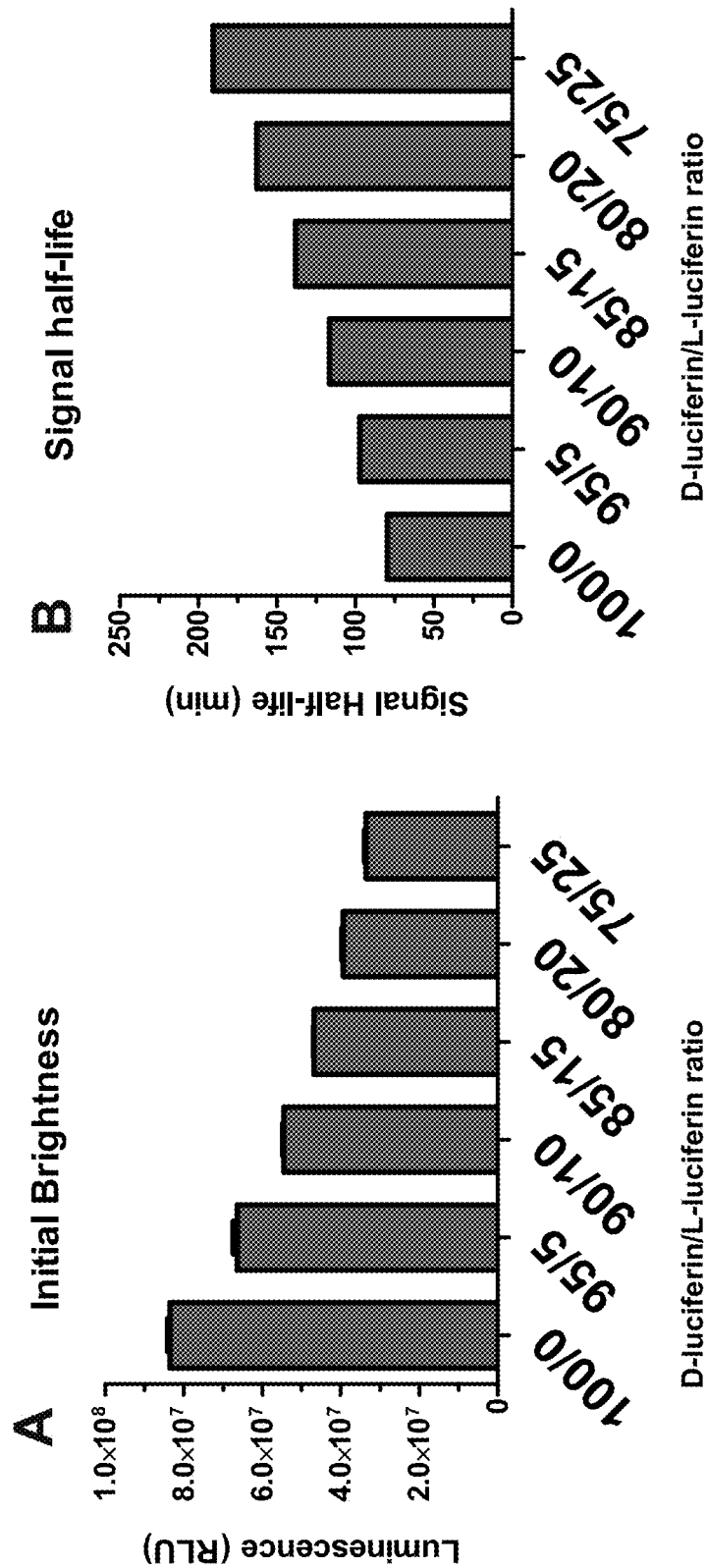
FIG. 4 shows graphs depicting the effect of different D-/L-luciferin (5'-fluoroluciferin) ratios in luciferase reporter assay reagents on luminescence (4A) and signal half-life (4B).

FIG. 4 demonstrates the effect of the different D-/L-luciferin ratios on initial luminescence (RLUs) (A) and signal half-life (B). The signal half-life was calculated by fitting the luminescence to a single exponential decay.

EXAMPLE 6

Effect of Different D-/L-luciferin Ratios on the Stability of a Luciferase Reporter Assay Reagent Firefly luciferase reporter assay reagents were made with varying ratios of D-/L-5'-fluoroluciferin (100:0; 90:10; 80:20; 70:30; 60:40; and 50:50). Each reagent was dispensed into 180 µl aliquots and incubated in a 22° C. water bath for varying amounts of time (0, 1, 2, 3, 4 or 5 days). After each time period, an aliquot of reagent with each ratio was frozen at −80° C. After the time course was finished, all aliquots were thawed, mixed by pipetting up and down, and 50 µl transferred to triplicate wells of a 96-well plate, which was then equilibrated at 22° C. Purified firefly luciferase (QuantiLum) was diluted to 0.69 µg/ml in DMEM supplemented with 0.1% Prionex, and 50 µl was added to each well and mixed for 3 minutes. Luminescence was read on a GloMax® Multi+ luminometer.

FIG. 5 shows enhanced room temperature stability of the luciferase reporter assay reagent as the ratio of D-/L-5'fluoroluciferin gets closer to 50:50.

What is claimed is:

1. A luciferase reaction composition for detecting luciferase activity, the composition comprising, a mixture of a concentration of l-luciferin and a concentration of D-luciferin, wherein the concentration of L-luciferin exceeds the concentration of D-luciferin, and the ratio of L-luciferin to D-luciferin is less than about 2:1, wherein the composition retains at least about 50% of the original activity in a luciferase reaction after being stored for at least about 5 days at a temperature from about 0° C. to about 35° C., and the concentration of L-luciferin in the mixture is at least about 100 µM.

2. The composition of claim 1, further comprising luciferase, wherein the composition is substantially free of adenosine triphosphate (ATP).

3. The composition of claim 1, further comprising adenosine triphosphate (ATP), wherein the composition is essentially free of luciferase.

4. The composition of claim 2, further comprising ATP.

5. The composition of claim 2, wherein the composition has a pH of at least about 5 and less than about 9.

6. The composition of claim 2, wherein the luciferase is a beetle luciferase.

7. The composition of claim 2, wherein the D-Luciferin is D-5'fluoroluciferin and the L-luciferin is L-5'fluoroluciferin.

8. A kit comprising the composition of claim 2.

9. The kit of claim 8, wherein the composition has increased storage-life and stability when stored at a temperature from about 0° C. to about 35° C. compared to a composition that has substantially no L-luciferin.

10. A method for determining the presence or amount of ATP in a sample comprising contacting the composition of claim 2 with a sample and detecting luminescence generated, thereby determining the presence or amount of ATP in the sample.

11. The method of claim 10, wherein the composition has increased storage-life and stability compared when stored at a temperature between about 0° C. to about 35° C. compared to a composition that has substantially no L-luciferin.

12. The composition of claim 6, wherein the beetle luciferase is a firefly luciferase.

13. The kit of claim 8, wherein the composition has increased storage-life when stored at a temperature from about 0° C. to about 35° C. compared to a composition that has substantially no L-luciferin.

14. The kit of claim 8, wherein the composition has increased stability when stored at a temperature from about 0° C. to about 35° C. compared to a composition that has substantially no L-luciferin.

15. The method of claim 10, wherein the composition has increased storage-life when stored at a temperature from about 0° C. to about 35° C. compared to a composition that has substantially no L-luciferin.

16. The method of claim 10, wherein the composition has increased stability when stored at a temperature from about 0° C. to about 35° C. compared to a composition that has substantially no L-luciferin.

* * * * *